(12) United States Patent
Yang et al.

(10) Patent No.: US 11,896,167 B2
(45) Date of Patent: Feb. 13, 2024

(54) PORTABLE TOWEL DRYER

(71) Applicant: SHENZHEN ANTOP TECHNOLOGY CO., LTD, Shenzhen (CN)

(72) Inventors: Ruidian Yang, Shenzhen (CN); Xianquan Liao, Shenzhen (CN)

(73) Assignee: SHENZHEN ANTOP TECHNOLOGY CO., LTD, Shenzhen (CN)

(*) Notice: Subject to any disclaimer, the term of this patent is extended or adjusted under 35 U.S.C. 154(b) by 649 days.

(21) Appl. No.: 17/119,217

(22) Filed: Dec. 11, 2020

(65) Prior Publication Data

US 2022/0095853 A1      Mar. 31, 2022

(30) Foreign Application Priority Data

Sep. 30, 2020 (CN) .......................... 202022223111.2

(51) Int. Cl.
*A47K 10/06* (2006.01)
*A61L 2/10* (2006.01)

(52) U.S. Cl.
CPC ................ *A47K 10/06* (2013.01); *A61L 2/10* (2013.01)

(58) Field of Classification Search
CPC ....... A47B 46/00; A47B 46/005; A47B 57/30; A47F 5/0081; A47F 5/08; A47F 7/19; A47K 10/06; A61L 2/10; A61L 2202/16; A61L 2202/23

USPC ............ 34/621; 211/173, 174, 207, 208, 16, 211/88.04, 90.02, 103, 117
See application file for complete search history.

(56) References Cited

FOREIGN PATENT DOCUMENTS

| CN | 107334412 A | * | 11/2017 |
| CN | 112021977 A | * | 12/2020 |
| CN | 212591850   | * | 2/2021  |
| CN | 212591850 U | * | 2/2021  |

* cited by examiner

*Primary Examiner* — John P McCormack
(74) *Attorney, Agent, or Firm* — SOROKER AGMON NORDMAN PTE LTD

(57) ABSTRACT

A portable towel dryer is provided in the present application, which comprises a main machine and a rack configured to hang a cloth, wherein the main machine comprises a shell, a heater mounted in the shell and a fan mounted in the shell, an air outlet is provided at a bottom of the shell corresponding to an outlet of the fan, the bottom of the shell is provided with an air inlet, and the heater is arranged on an airflow path of the fan, wherein the rack comprises a hanging rod, two supports respectively supporting both ends of the hanging rod, and a lifting mechanism configured to adjust the height of the supports, each of the supports is connected with the lifting mechanism, and the lifting mechanism is connected with the shell.

17 Claims, 8 Drawing Sheets

PORTABLE TOWEL DRYER

CROSS-REFERENCE TO RELATED APPLICATIONS

This application claims priority to Chinese Patent Application No. 202022223111.2 filed on Sep. 30, 2020, the content of which is incorporated herein by reference thereto.

TECHNICAL FIELD

The present application relates to the field of dryers, and more specifically relates to a portable towel dryer.

BACKGROUND

Towel dryers are devices generally used to dry cloth such as a towel, clothing and the like in order to prevent the cloth being moldy and facilitate a user to use. The existing towel dryers usually arrange a heater in a main machine to heat the cloth on a drying rack. At present, the towel dryers are divided into two types, one is a structure with the rack and the main machine separated and the rack and the main machine are respectively mounted on the wall, which is inconvenient to mount; the other is an integrated towel dryer with the rack connected to the main machine, the rack is mounted at the bottom of the main machine and then only the main machine is required to be fixed. However, due to the fact that a hanging rod of the rack is close to the main machine regarding the integrated towel dryer, it is easy to bruise the user's hand when taking out and placing the cloth, which is not convenient to use.

SUMMARY

A purpose of embodiments of the present application is intended to provide a portable towel dryer, in order to solve the technical problem existed in related technologies that integrated towel dryers are easy to bruise the user's hand when taking out and placing the cloth due to the fact that the hanging rod of the rack is close to the main machine and are inconvenient to use.

In order to realize the above purpose, technical solutions adopted by the present application is as follow: a portable towel dryer is provided, which comprises a main machine and a rack configured to hang a cloth, wherein the main machine comprises a shell, a heater mounted in the shell and a fan mounted in the shell, an air outlet is provided at a bottom of the shell corresponding to an outlet of the fan, the bottom of the shell is provided with an air inlet, and the heater is arranged on an airflow path of the fan, wherein the rack comprises a hanging rod, two supports respectively supporting both ends of the hanging rod, and a lifting mechanism configured to adjust the height of the supports, each of the supports is connected with the lifting mechanism, and the lifting mechanism is connected with the shell.

In an optional embodiment, the lifting mechanism comprises a reinforcing plate connected with each of the supports respectively and a locking component configured to lock the reinforcing plate in the shell, the locking component is mounted on the shell, an upper end of the reinforcing plate is slidably inserted into the shell, and the bottom of the shell is provided with a jack for slidable insertion of an upper end of the reinforcing plate therein.

In an optional embodiment, the reinforcing plate is provided with a plurality of clamping slots, and the plurality of clamping slots are distributed on the reinforcing plate along a vertical direction at an interval; the locking component comprises a latch configured to fit into the clamping slot, a supporting shaft configured to support the latch, a supporting block configured to support the supporting shaft, and an elastic member configured to elastically push the latch along an axial direction of the supporting shaft into the clamping slot, the elastic member is mounted in the supporting block, and the supporting block is mounted on the shell.

In an optional embodiment, the locking component further comprises a button configured to push the latch, the button is mounted on the supporting block, and the button and the elastic member are respectively located on the opposite sides of the latch.

In an optional embodiment, the supporting block is arranged in the shell, and the shell is provided with a through hole configured to expose the button.

In an optional embodiment, a receiving groove is arranged in the supporting block, the latch is located in the receiving groove, and opposite two side walls of the receiving groove support the two ends of the supporting shaft respectively.

In an optional embodiment, each of the supports is provided with a support section, and a vertical section configured to support a wall, a lower end of the vertical section is fixedly connected with a rear end of the support section, the end of the hanging rod is supported on the corresponding support section, an upper end of the reinforcing plate extends out the vertical section, and each of the jacks is located at a corresponding position close to a rear side of shell.

In an optional embodiment, the support section is arranged as inclined downward in a direction from the rear side of the shell to a front side of the shell.

In an optional embodiment, the main machine further comprises an ultraviolet light source, and the ultraviolet light source is supported on the shell.

In an optional embodiment, the ultraviolet light source is an ultraviolet lamp tube, the main machine further comprises a lamp holder mounted in the shell, and a window exposing the ultraviolet lamp tube is arranged at the bottom of the shell.

The beneficial effects of the portable towel dryer provided by the embodiments of the present application lie in that: compared with the prior art, in the portable towel dryer of the present application, the supports are arranged to support the hanging rod, and the lifting mechanism is arranged to support the supports, and the lifting mechanism is connected with the shell, then the height of the supports can be adjusted through the lifting mechanism, so that the support can be lowered when taking out and placing the cloth, while the support can be raised when drying the cloth to facilitate use.

Further areas of applicability will become apparent from the description provided herein. The description and specific examples in this summary are intended for purposes of illustration only and are not intended to limit the scope of the present disclosure.

DESCRIPTION OF THE DRAWINGS

In order to more clearly illustrate the technical solutions in the embodiments of the present application, the drawings needed to be used in the description for the embodiments or exemplary technologies are briefly introduced below. Obviously, the drawings in the following description are only some embodiments of the present application, and other drawings may also be obtained based on these drawings for those skilled in the art without paying creative labor.

Figure 1:
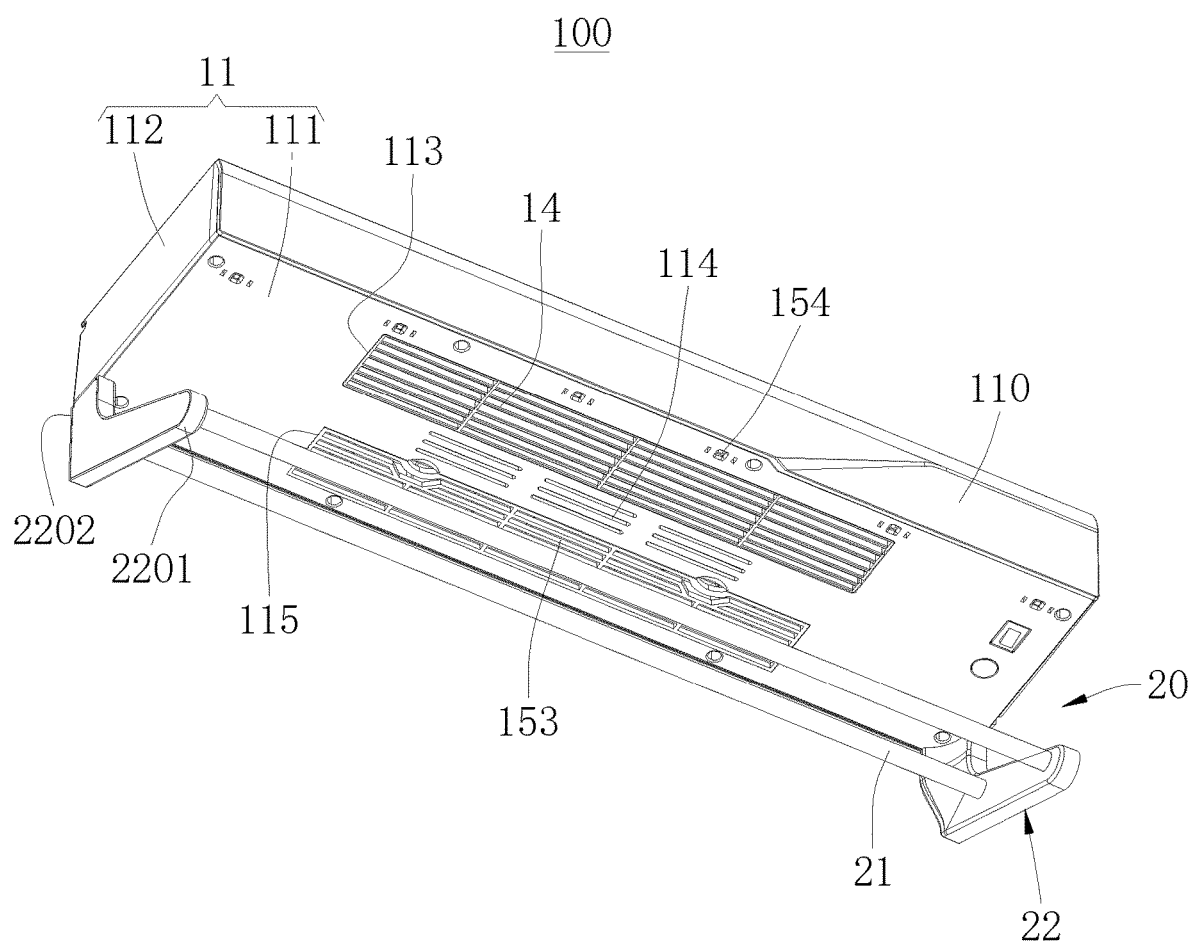
FIG. 1 is a structural diagram of the portable towel dryer provided by an embodiment of the present application.

Among them, main reference signs in the drawings are as follows:

100—portable towel dryer; 10—main machine; 11—shell; 110—control panel; 111—baseplate; 112—cover; 1120—through hole; 1121—buckle; 1122—hidden wire slot; 113—air outlet; 114—air inlet; 115—window; 116—jack; 12—heater; 121—heating plate; 122—cooling fin; 13—fan; 131—fan housing; 132—tubular wind wheel; 133—motor; 14—air guide window; 151—ultraviolet lamp tube; 152—lamp holder; 153—grille window; 154—ultraviolet LED module; 16 reflector; 161 support plate; 162 reflective side plate; 163 airflow hole;

20—rack; 21—hanging rod; 22—support; 2201—support section; 2202—vertical section; 2203—support hole; 221—fixed casing; 2211—receiving cavity; 2212—opening; 2213—positioning column; 2214—reinforcing rib; 222—cover casing; 23—lifting mechanism; 231—reinforcing plate; 2311—clamping slot; 2312—positioning hole; 232—locking component; 2321—latch; 2322—supporting shaft; 2323—supporting block; 23231—receiving groove; 2324—elastic member; 2325 button;

900—wall.

Corresponding reference numerals indicate corresponding parts throughout the several views of the drawings.

DETAILED EMBODIMENTS

In order to make the technical problems to be solved, technical solutions and beneficial effects of the present application more clearly and comprehensibly, the present application is further described in detail in combination with the drawings and embodiments. It should be understood that the specific embodiments described herein are only for the purpose of illustrating the present application and are not intended to limit the present application.

The reference to "one embodiment", "some embodiments" or "an embodiment" described in the specification of the present application means that a specific feature, structure, or characteristic described in connection with this embodiment is included in one or more embodiments of the present application. Therefore, the statements "In an embodiment", "in some embodiments", "in some other embodiments", "in other embodiments" and so on appearing in different places of the specification do not necessarily refer to the same embodiment, but mean "one or more, but not all embodiments", unless otherwise specially emphasized. Further, in one or more embodiments, the specific features, structures or characteristics may be combined in a any suitable manner.

The Chinese term and English term corresponding to the English abbreviation which is used in the present application is as follows:

LED, English: Light Emitting Diode; Chinese: Light Emitting Diode.

Figure 2:
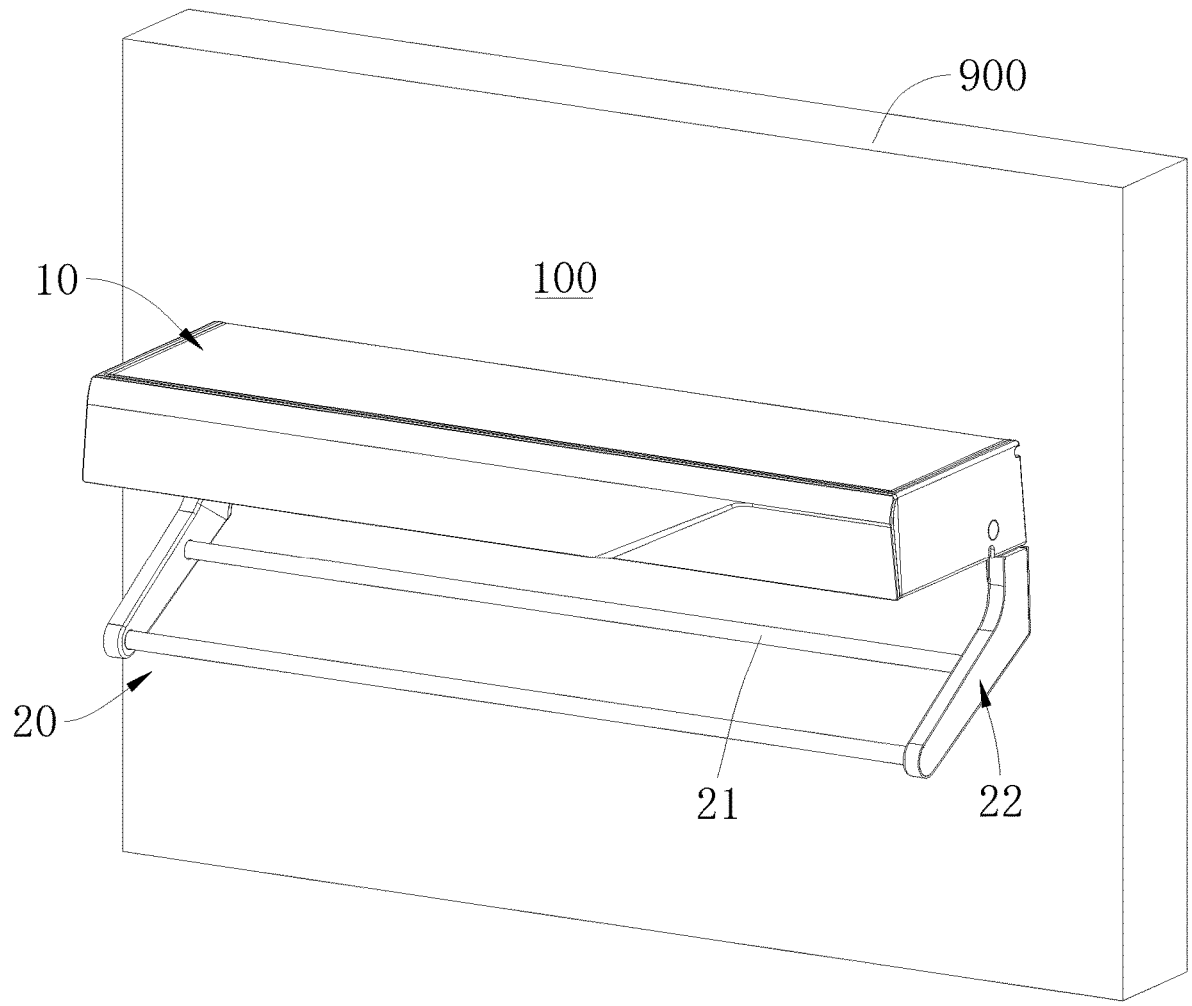
FIG. 2 is a structural diagram of the portable towel dryer mounted on a wall provided by an embodiment of the present application.

For the convenience of description, please refer to FIG. 1 and FIG. 2. It is defined in the present application that, when the main machine 10 is mounted on the wall 900, a side of the main machine 10 close to the wall 900 is a rear side of the main machine 10, the shell 11 and the portable towel dryer 100, while a side of the main machine 10 facing away from the wall 900 is a front side of the main machine 10, the shell 11 and the portable towel dryer 100.

Figure 3:
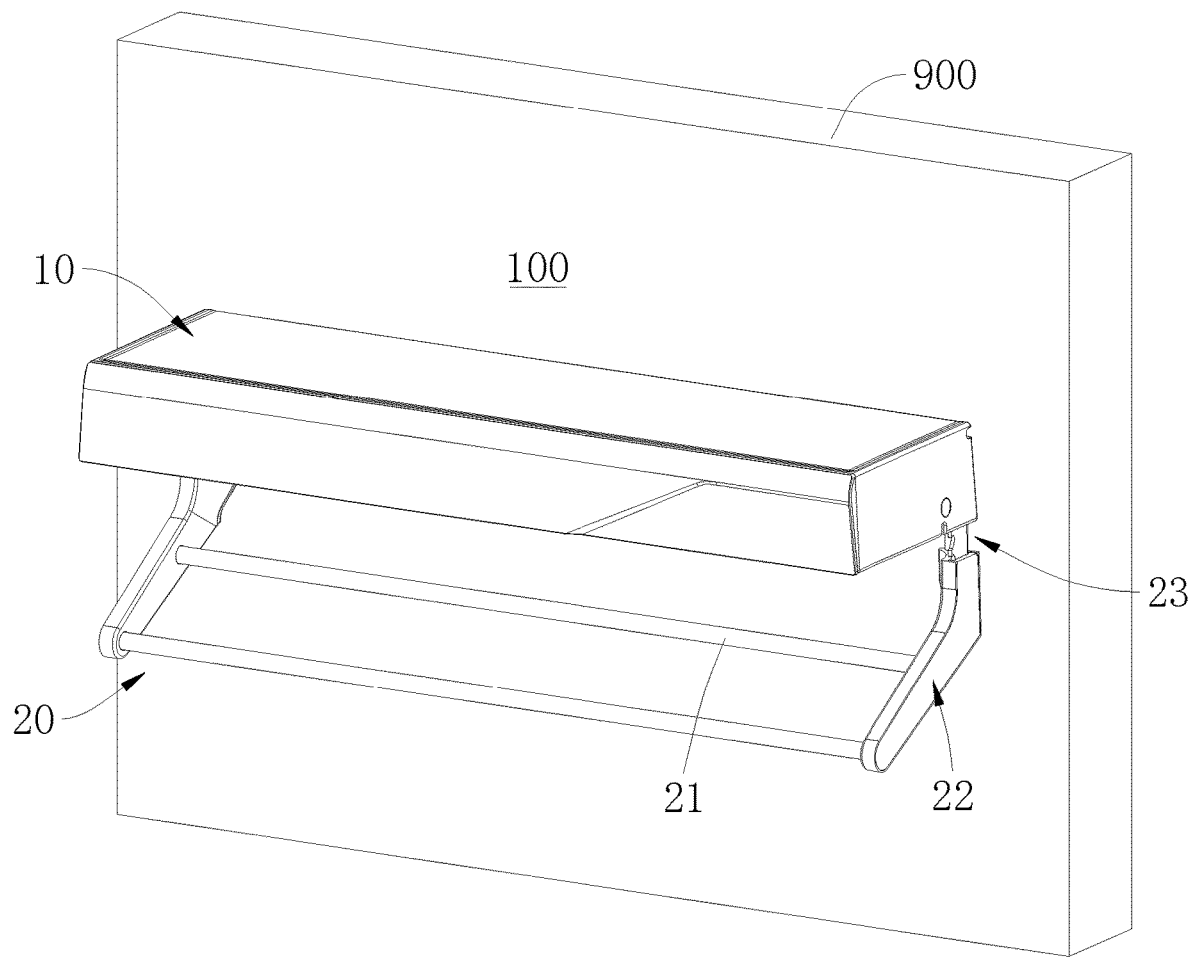
FIG. 3 is a structural diagram of the portable towel dryer as shown in FIG. 2 after the height of a support thereof is lowered.
Figure 7:
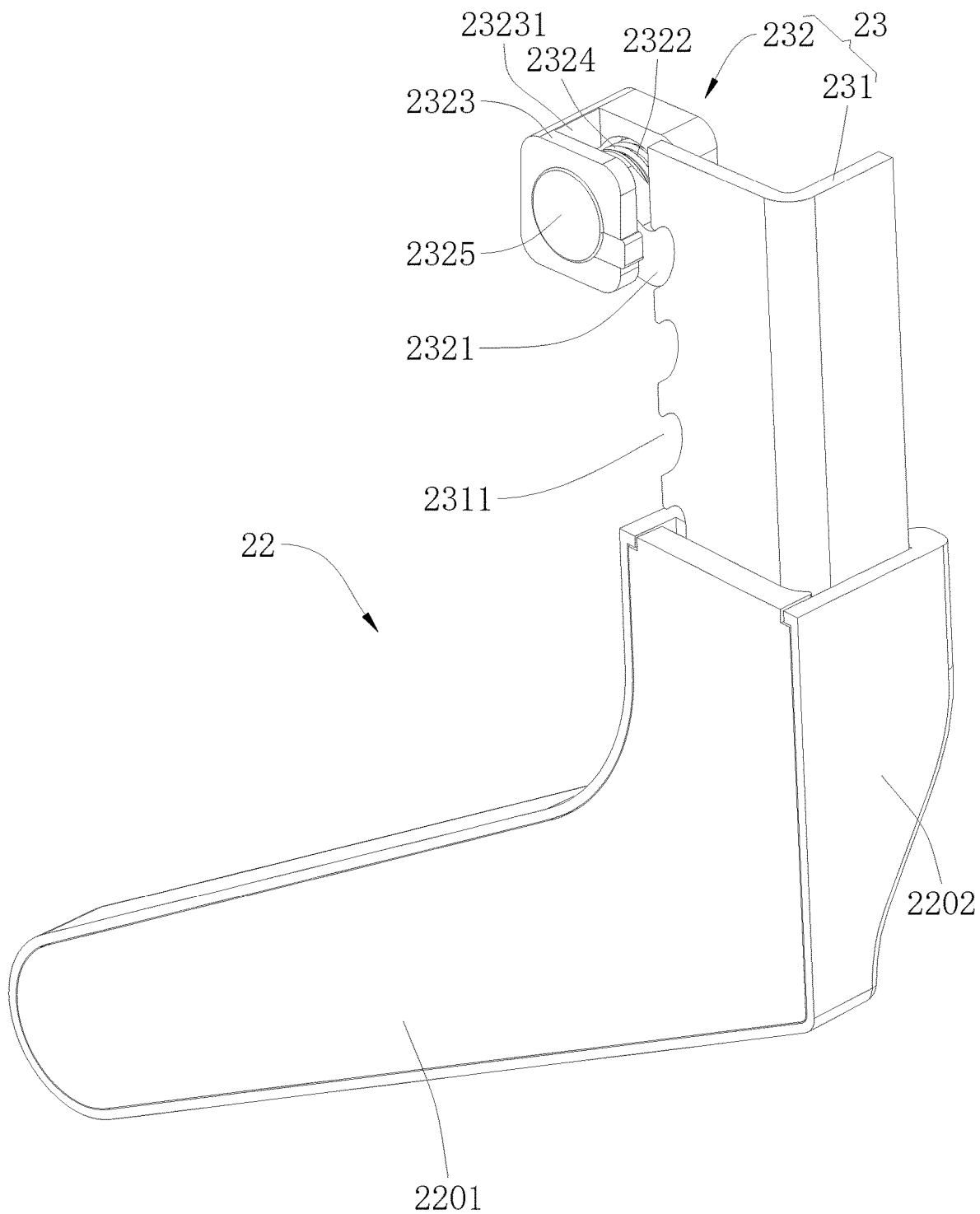
FIG. 7 is a structural diagram of a support and a lifting mechanism in FIG. 6.

Please refer to FIG. 1, FIG. 3 and FIG. 7, the portable towel dryer 100 provided by the present application is now illustrated. The portable towel dryer 100 includes a main machine 10 and a rack 20, the rack 20 is configured to hang a cloth, that is, the cloth such as a towel and the like may be hung on the rack 20, while the main machine 10 is arranged above the rack 20, such that the cloth on the rack 20 is heated and dried through the main machine 10. The rack 20 may be supported at a bottom of a shell 11 to integrate the rack 20 and the main machine 10, so as to facilitate installation and use.

Figure 4:
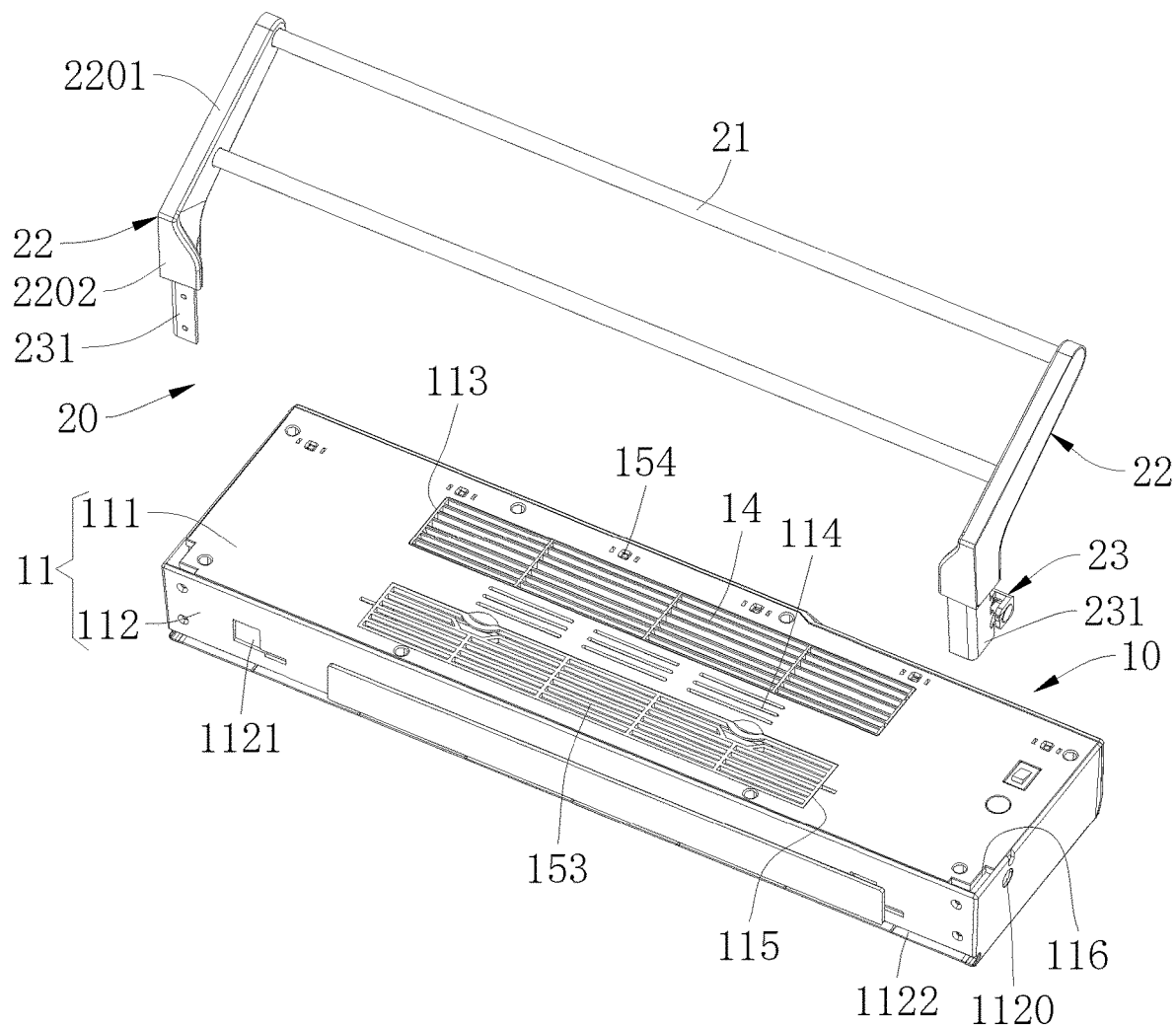
FIG. 4 is an exploded structure diagram of the portable towel dryer provided by an embodiment of the application.
Figure 5:
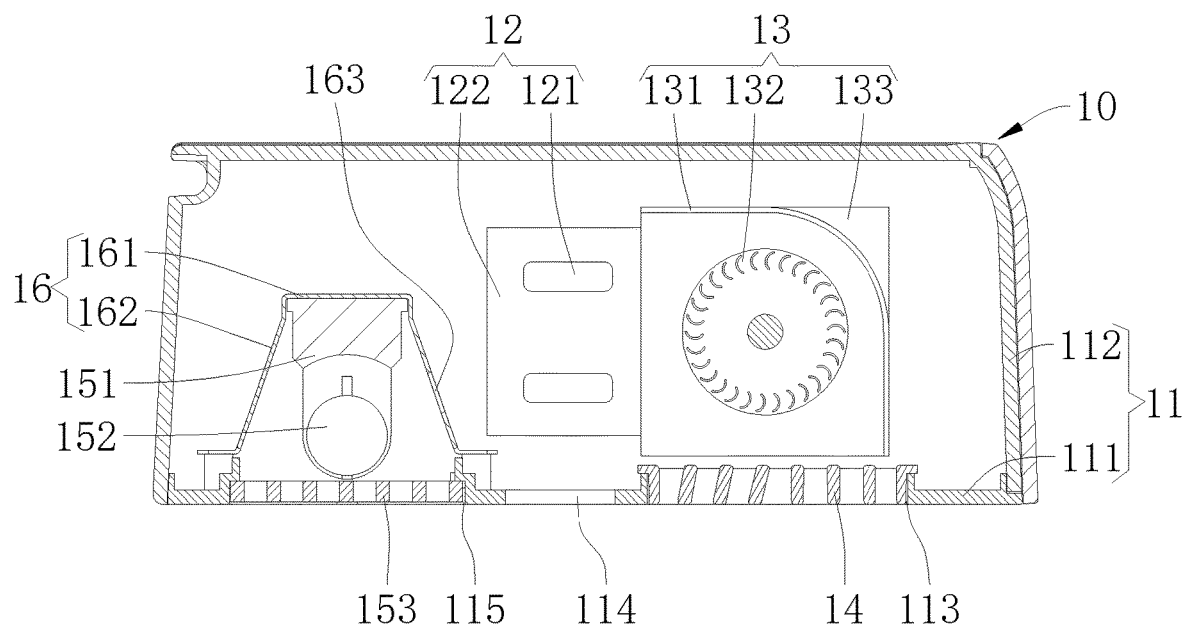
FIG. 5 is a sectional structure diagram of a main machine in FIG. 4.

Please refer to FIG. 4 and FIG. 5, the main machine 10 includes a shell 11, a heater 12, and a fan 13, the heater 12 and the fan 13 are mounted in the shell 11, so that the heater 12 and the fan 13 is protected through the shell 11. The heater 12 is arranged at an airflow path of the fan 13. The heater 12 is used to heat air, and the fan 13 blows out the heated air to dry the cloth. An air outlet 113 and an air inlet 114 are arranged at a bottom of the shell 11, and the air outlet 113 is located at an outlet of the fan 13 to blow out the airflow.

Figure 6:
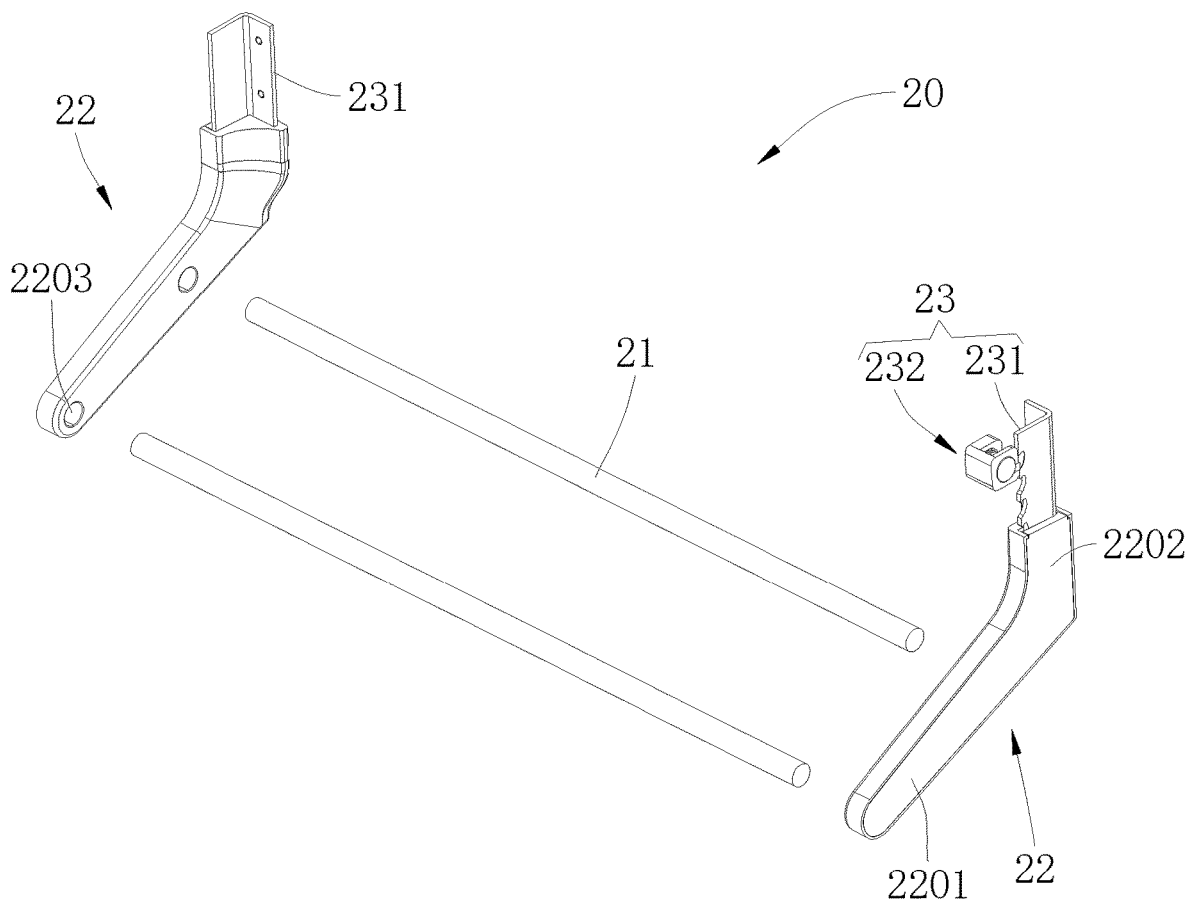
FIG. 6 is an exploded structure diagram of a rack in FIG. 4.

Please refer to FIG. 3, FIG. 6 and FIG. 7, the rack 20 includes a hanging rod 21, two supports 22, and a lifting mechanism 23. The two supports 22 respectively support both ends of the hanging rod 21 to support the hanging rod 21, and then the cloth such as the towel and the like may be placed on the hanging rod 21. The lifting mechanism 23 is connected with the shell 11, and the supports 22 are mounted on the lifting mechanism 23 and supported by the lifting mechanism 23, and the supports 22 are supported on the shell 11 to further support the hanging rod 21. The height of the supports 22 are adjusted through the lifting mechanism 23, and then the height of the hanging rod 21 is adjusted. The heights of the supports 22 and the hanging rod 21 are lowered when the cloth is taken out and placed, so as to conveniently take out the cloth from the hanging rod 21; it is also convenient to place an article needing to be dried on the hanging rod 21, and then the heights of the supports 22 and the hanging rod 21 are raised, so as to dry the article on the hanging rod 21.

In the portable towel dryer 100 provided by the present application compared with the prior art, the hanging rod 21 is supported by arranging the supports 22, the supports 22 are supported by arranging the lifting mechanism 23, and the lifting mechanism 23 is connected with the shell 11, then the portable towel dryer 100 in the present application can adjust the height of the supports 22 by the lifting mechanism 23, such that the height of the supports 22 can be lowered when taking out and placing the cloth, while the height of the supports 22 can be raised when drying the cloth, thereby facilitating use.

In an embodiment, please refer to FIG. 3, FIG. 4 and FIG. 7, the lifting mechanism 23 includes two reinforcing plates 231 and a locking component 232, the two reinforcing plates 231 are respectively connected with the two supports 22, and the corresponding supports 22 are supported by the reinforcing plates 231. The bottom of the shell 11 is provided with a jack 116, an upper end of the reinforcing plate 231 is slidably inserted into the corresponding jack 116, the locking component 232 is mounted on the shell 11, and the locking component 232 is configured to lock the reinforcing plates 231 in the shell 11 to fix the reinforcing plates 231 and further lock the height of the reinforcing plates 231, so as to position the height of the supports 22. By using the reinforcing plates 231, the supports 22 can be stably supported, and the strength of the rack 20 can be increased, such that the rack 20 can be fixedly connected with the shell 11. In some embodiments, the lifting mechanism 23 may also adopt a lifting rope structure. In some other embodiments, the lifting mechanism 23 may also adopt a telescopic rod, and the supports 22 are connected with the shell 11 through the telescopic rod, thereby realizing the lifting adjustment of the supports 22.

In an embodiment, the reinforcing plate 231 is provided with a plurality of clamping slots 2311, and the plurality of clamping slots 2311 are vertically distributed on the reinforcing plate 231 at an interval. The locking component 232 includes a latch 2321, a supporting shaft 2322, a supporting block 2323, and an elastic member 2324. The latch 2321 is configured to fit into the corresponding clamping slot 2311 to lock the reinforcing plate 231. The latch 2321 is mounted on the supporting shaft 2322, and the latch 2321 is supported through the supporting shaft 2322. The supporting shaft 2322 is mounted on the supporting block 2323 and supported through the supporting block 2323, and then the latch 2321 is supported. The elastic member 2324 is mounted in the supporting block 2323, and the elastic member 2324 is configured to elastically push the latch 2321 along an axial direction of the supporting shaft 2322, so that the latch 2321 is extended into the corresponding clamping slot 2311 of the reinforcing plate 231 to position the reinforcing plate 231. Further, the latch 2321 may be pushed out of the clamping slot 2311 to unlock the reinforcing plate 231 so as to adjust the height of the reinforcing plate 231. In some other embodiments, the locking component 232 may also be a claw structure mounted on the shell 11, and the claw may be fitted into the clamping slot 2311 by rotating the claw to position the reinforcing plate 231. In still some embodiments, the reinforcing plate 231 may also be provided with a locking hole, and the reinforcing plate 231 may be locked through mating a hoodle with the locking hole.

In an embodiment, there may be one locking component 232, and correspondingly the clamping slot 2311 may be provided on the one reinforcing plate 231. Of course, there may be one locking components 232, and the clamping slots 2311 may be arranged on the two reinforcing plates 231 respectively. In some other embodiments, there may be two locking components 232, the clamping slots 2311 may be arranged on the two reinforcing plates 231 respectively, and the two locking components 232 correspond to the two reinforcing plates 231 respectively.

In an embodiment, the elastic member 2324 may be a spring. In some other embodiments, the elastic member 2324 may also be a shrapnel or the like.

In an embodiment, please refer to FIG. 4 and FIG. 7, the locking component 232 further includes a button 2325, which is mounted on the supporting block 2323, and the latch 2321 may be pushed by the button 2325 to move along the supporting shaft 2322. The button 2325 and the elastic member 2324 are respectively located on opposite sides of the latch 2321, so that the latch 2321 may be pushed out of the clamping slot 2311 of the reinforcing plate 231 to unlock the reinforcing plate 231.

In an embodiment, the supporting block 2323 is arranged in the shell 11, and the shell 11 is provided with an through hole 1120 to expose the button 2325, so as to protect the locking component 232 through the shell 11 and facilitate the pressing of the button 2325, and then the appearance of the main machine 10 is improved.

In an embodiment, the latch 2321 may be rotatably mounted on the supporting shaft 2322, and the locking component 232 further includes an elastic block (not shown in the figure). The elastic block is arranged on a lower side of the latch 2321 and configured to elastically push the latch 2321 upward. The lower side surface of the latch 2321 is a curved surface extending along an orientation from the supporting shaft 2322 to a direction facing away from the supporting shaft 2322, so that the lower side surface of the latch 2321 may play a role of guiding. When the reinforcing plate 231 is pushed upward, the latch 2321 may rotate upward so that the reinforcing plate 231 may rise; when the reinforcing plate 231 needs to be lowered, it is necessary to push the latch 2321 out of the clamping slot 2311.

In an embodiment, the supporting block 2323 is provided with a receiving groove 23231, and the latch 2321 is located in the receiving groove 23231. Two opposite side walls of the receiving groove 23231 support two ends of the supporting shaft 2322 respectively, so that the supporting shaft 2322 can be supported more stably, and the latch 2321 can be better protected.

In an embodiment, please refer to FIG. 1 and FIG. 7, each of the supports 22 has a support section 2201 and a vertical section 2202, a lower end of the vertical section 2202 is fixedly connected with a rear end of the support section 2201, the end of the hanging rod 21 is supported on the corresponding support section 2201, the vertical section 2202 is fixedly connected with the reinforcing plate 231, and the upper end of the reinforcing plate 231 extends out of the vertical section 2202, and each jack 116 is located at a corresponding position close to the rear side of the shell 11 Therefore, when the shell 11 is mounted on the wall 900, the vertical section 2202 of the support 22 may be supported against the wall 900, so that the lower end of the vertical section 2202 will form a fulcrum with the wall 900 when the cloth is placed on the hanging rod 21, that is to say, the wall 900 will be used as a rear fulcrum for the rack 20 to bear a larger weight, the area stressed on the wall 900 may be increased, and the firmness of the connection may be increased, so that the weight of the shell 11 may be reduced to stably support the rack 20, and the structure of the shell 11 is further simplified since there is no need to arrange a metal plate in the shell 11, thereby reducing the weight and the cost of the shell 11.

In an embodiment, there are at least two the hanging rods 21, and adjacent two hanging rods 21 are arranged in parallel, so that more cloth such as towels can be placed.

In an embodiment, please refer to FIG. 1, FIG. 2 and FIG. 6, the support section 2201 is arranged downward in the direction from the rear side of the shell 11 to the front side of the shell 11, that is, the height of the rear end of the support section 2201 is greater than the height of the front end of the support section 2201, this structure can facilitate placing the cloth such as the towel and the like on the hanging rod 21.

In an embodiment, in the two adjacent hanging rods 21, the height of the hanging rod 21 close to the front side of the shell 11 is lower than the height of the hanging rod 21 close to the rear side of the shell 11, so that the distance between the front hanging rod 21 and the shell 11 is larger, while the distance between the back hanging rod 21 and the shell 11 is small, thereby facilitating placement of the cloth on each of the hanging rods 21.

In an embodiment, an angle range between the support section 2201 of the support 22 and the horizontal direction is 10~45 degrees, so that a good height difference can be formed between the two adjacent hanging rods 21 supported by the two support sections 2201, and there is a relatively large space in the horizontal direction, so as to facilitate the placement of the cloth on each of the hanging rods 21. However, if the angle between the support section 2201 and the horizontal direction is less than 10 degrees, the height difference between the two adjacent hanging rods 21 will be relatively small, and then it is difficult to place the cloth on the hanging rods 21. If the angle between the support section 2201 and the horizontal direction is greater than 45 degrees, the height difference between the two adjacent hanging rods 21 will be too large, such that a large space is occupied by the portable towel dryer 100, and the main machine 10 needs to be arranged at a relatively high place, and the distance between the two adjacent hanging rods 21 is too close in the horizontal direction, thereby the cloth on the two adjacent hanging rods 21 will block each other.

Figure 8:
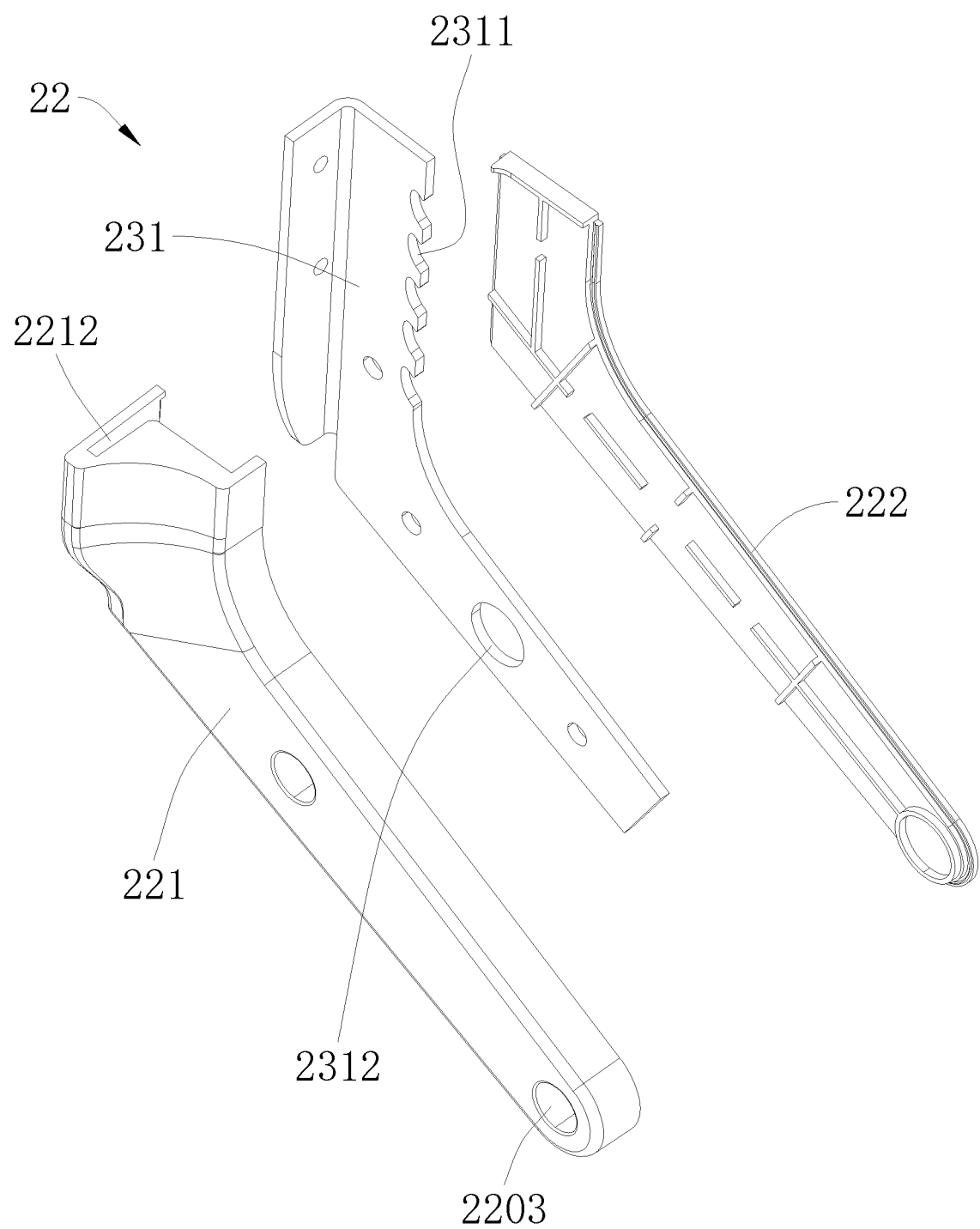
FIG. 8 is a first exploded structure diagram of the support and a reinforcing plate in FIG. 7.
Figure 9:
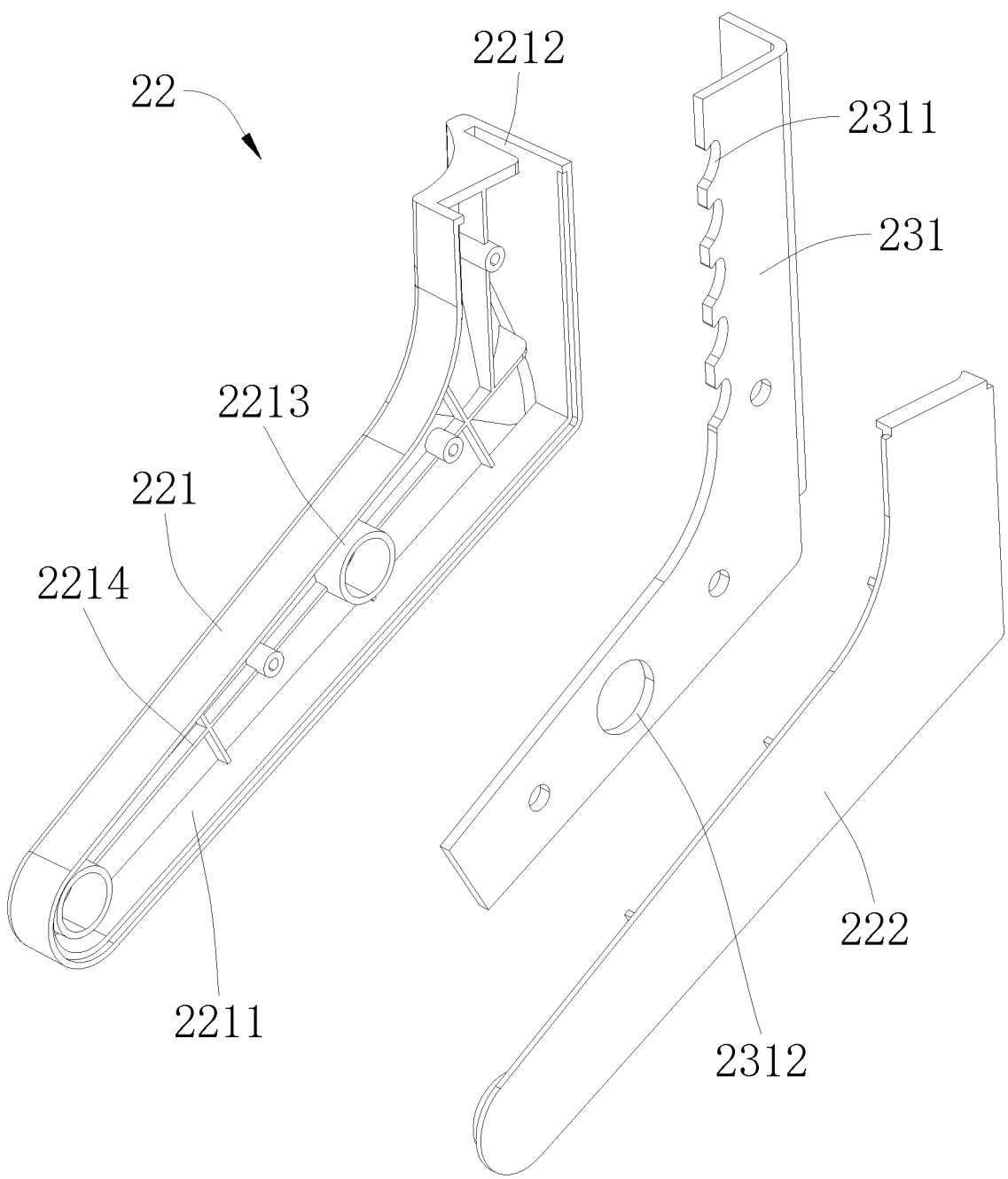
FIG. 9 is a second exploded structure diagram of the support and the reinforcing plate in FIG. 7.

In an embodiment, please refer to FIG. 4, FIG. 8 and FIG. 9, the lower end of the reinforcing plate 231 extends into the support section 2201 to ensure the good strength of the support 22. In addition, since the support section 2201 is inclined to the vertical section 2202, the reinforcing plate 231 may be more firmly connected with the support 22.

In an embodiment, the cross section of the reinforcing plate 231 is L-shaped, which can ensure the good strength of the reinforcing plate 231. Two corners of the rear side of the bottom of the shell 11 are respectively provided with jacks 116, and the cross-section of each jack 116 is L-shaped, so that the reinforcing plate 231 can be positioned and fixed.

In an embodiment, the jacks 116 may be respectively provided at two corners of the rear side of the bottom plate of the shell 11, so that when inserted into the corresponding jack 116, the reinforcing plate 231 may be connected with the rear side wall of the cover of the shell 11.

In an embodiment, please refer to FIG. 8 and FIG. 9, the support 22 includes a fixed casing 221 and a cover casing 222, the fixed casing 221 is provided with a receiving cavity 2211, the lower end of the reinforcing plate 231 is arranged in the receiving cavity 2211, the fixed casing 221 is provided with an opening 2212, the upper end of the reinforcing plate 231 extends from the opening 2212 of the fixed casing 221, and the cover casing 222 covers the fixed casing 221 to fix the reinforcing plate 231 through mating the fixed casing 221. The structure of the support 22 is convenient for processing and easy to be mounted on the fixed reinforcing plate 231.

In an embodiment, the support section 2201 of the support 22 is provided with a support hole 2203 to facilitate the positioning and supporting of the hanging rod 21. Specifically, the support hole 2203 may be arranged on the fixed casing 221 to support the hanging rod 21.

In an embodiment, the receiving cavity 2211 of the fixed casing 221 is provided with a positioning column 2213, a positioning hole 2312 is arranged on the reinforcing plate 231, and the positioning column 2213 is inserted into the positioning hole 2312 such that the reinforcing plate 231 may be positioned. When the cover casing 222 is connected with the fixed casing 221, the reinforcing plate 231 may be fixed in the fixed casing 221.

In an embodiment, the receiving cavity 2211 of the fixed casing 221 is provided with a reinforcing rib 2214 to ensure the good strength of the fixed casing 221, and the weight of the support 22 can also be reduced as well as the cost is reduced.

In an embodiment, the reinforcing plate 231 may adopt a metal plate to ensure the good strength of the reinforcing plate 231. Of course, in some embodiments, the reinforcing plate 231 may also be made of other high-strength material.

In some embodiments, the reinforcing plate 231 and the support 22 may be molded into an integral structure to ensure the connection strength of the support 22 and the reinforcing plate 231.

In an embodiment, please refer to FIG. 1 and FIG. 5, the heater 12 may be arranged at an inlet of the fan 13, then the air will be heated by heater 12 and then blown out after inhaled and accelerated by the fan 13. Due to the relatively small airflow velocity at the inlet of the fan 13, the air may be fully heated by the heater 12 before entering the fan 13, so the heat utilization rate is high, and the power of the corresponding heater 12 may be made lower. In other embodiments, the heater 12 may also be arranged at an outlet of the fan 13, so the airflow blown out by the fan 13 is heated by the heater 12 and then flows out.

In an embodiment, the fan 13 includes a fan housing 131, a tubular wind wheel 132 and a motor 133, and the motor 133 is connected with the tubular wind wheel 132 so that the tubular wind wheel 132 is driven to rotate through the motor 133. The tubular wind wheel 132 is mounted in the fan housing 131 to guide the airflow through the fan housing 131. By using the tubular wind wheel 132, the volume may be made smaller, and the air volume is large, so the volume of the main machine 10 may be made smaller. Of course, the fan 13 may also adopt other structures in some other embodiments.

In an embodiment, the heater 12 includes a heating plate 121 and a plurality of cooling fins 122, and the plurality of cooling fins 122 are arranged on the heating plate 121 to heat the air more efficiently and quickly. The use of the heating plate 121 has high safety. Of course, the heater 12 may also adopt a heating wire, a heating tube, etc in some other embodiments.

In an embodiment, the main machine 10 further includes a air guide window 14, which is mounted in the air outlet 113 to guide the airflow diffusion, that is, when the airflow blown out by the fan 13 passes through the air guide window 14, the airflow is guided by the air guide window 14 to better heat and dry the cloth.

In an embodiment, blinds may be used as the air guide window 14. In some other embodiments, the air guide window 14 may also adopt a guide plate to guide the airflow diffusion.

In an embodiment, please refer to FIG. 4, the rear side of the shell 11 is provided with a buckle 1121, so that the shell 11 may be mounted on the wall 900 by means of hanging, the installation and fixation of which are convenient. Of course, in some other embodiments, the shell 11 may be mounted on the wall 900 using screws.

In an embodiment, please refer to FIG. 4, a hidden wire slot 1122 is arranged on the rear side of the shell 11, so that the power supply may be placed in the hidden wire slot 1122.

In some embodiments, please refer to FIG. 1 and FIG. 5, the main machine 10 also includes an ultraviolet light source mounted on the shell 11 and emitting ultraviolet light, so as to disinfect the cloth on the rack 20.

In an embodiment, please refer to FIG. 1 and FIG. 5, the ultraviolet light source is an ultraviolet lamp tube 151, and the main machine 10 also includes a lamp holder 152. The lamp holder 152 is mounted in the shell 11, and the ultraviolet lamp tube 151 is mounted on the lamp holder 152. The lamp holder 152 supports the ultraviolet lamp tube 151 and supply power to the ultraviolet lamp tube 151 to facilitate the emission of the ultraviolet light by the ultraviolet lamp tube 151, thus disinfecting the cloth. The bottom of the shell 11 is provided with a window 115 located at a corresponding position of the lamp holder 152, so as to expose the ultraviolet lamp tube 151, so that the ultraviolet light emitted by the ultraviolet lamp tube 151 may be emitted. The ultraviolet lamp tube 151 has the advantages of convenient installation and low cost.

Of course, in some other embodiments, the ultraviolet light source may also be an ultraviolet LED module 154, the ultraviolet light is emitted through the ultraviolet LED module 154 to disinfect the cloth on the rack 20. When the ultraviolet light source is the ultraviolet LED module 154, the ultraviolet LED module 154 may be mounted on the bottom surface of the shell 11, alternatively the ultraviolet LED module 154 may be mounted inside the shell 11 and a light transmission hole is arranged on the bottom surface of the shell 11 to transmit the ultraviolet light emitted by the ultraviolet LED module 154.

In some other embodiments, the ultraviolet lamp tube 151 and the ultraviolet LED module 154 may be mounted on the shell 11 at the same time, so as to improve the area covered by the ultraviolet light and better disinfect the cloth on the rack 20.

In an embodiment, please refer to FIG. 1 and FIG. 5, the ultraviolet lamp tube 151 may be detachably mounted on the lamp holder 152 to facilitate the replacement of the ultraviolet lamp tube 151. In addition, when replacing the ultraviolet lamp tube 151, the hanging rod 21 can be rotated such that the hanging rod 21 is located at the front side of the shell 11, so that the hanging rod 21 may be far away from the ultraviolet lamp tube 151 so as to facilitate the replacement of the ultraviolet lamp tube 151.

In an embodiment, please refer to FIG. 1 and FIG. 5, the main machine 10 further includes a reflector 16 mounted in the shell 11. The reflector 16 covers the lamp holder 152, so that the reflector 16 may cover the ultraviolet lamp tube 151 when the ultraviolet lamp tube 151 is mounted on the lamp holder 152, so as to reflect the ultraviolet light emitted by the ultraviolet lamp tube 151 to a specified direction, thereby improving the utilization rate of the ultraviolet light, saving more energy. Moreover, it is avoided that the corresponding parts are aged due to illumination of the ultraviolet light emitted by the ultraviolet lamp tube 151 to other parts in the shell 11.

In an embodiment, please refer to FIG. 1 and FIG. 5, the shell 11 includes a base plate 111 and a cover 112 covered on the base plate 111, and the window 115 and the air outlet 113 are arranged on the base plate 111. The shell 11 is convenient for processing and manufacturing, and is also convenient for the mounting of the lamp holder 152, the ultraviolet lamp tube 151, the reflector 16, the heater 12 and the fan 13 in the shell 11. In an embodiment, the base plate 111 forms the bottom of the shell 11. Of course, in some other embodiments, when the lower end of the cover 112 is arranged around the base plate 111, the lower end of the peripheral side of the cover 112 and the base plate 111 constitute the bottom of the shell 11. In some embodiments, the shell 11 may also be assembled by using a plurality of plates.

In an embodiment, a control panel 110 is arranged on the front side of the shell 11, and the control panel 110 is inclined to the interior of the shell 11 from top to bottom, so as to facilitate the user to operate and determine the position of the control panel 110. In an embodiment, the control panel 110 is arranged on the cover 112 to facilitate processing.

In an embodiment, the window 115 is located at the position corresponding to the rear side of the bottom of the shell 11, so that the window 115 is closer to the wall 900 when in use and the ultraviolet lamp tube 151 is also closer to the wall 900, so as to better limit the range of the ultraviolet light and improve safety.

In an embodiment, the reflector 16 is located on an air inlet path of the fan 13, and the reflector 16 is provided with an airflow hole, so that the air will enter the reflector 16 through the window 115 and then enter the fan 13 from the airflow hole, so as to cool the lamp holder 152 and the ultraviolet lamp tube 151 in the reflector 16, thereby improving service life of the ultraviolet lamp tube 151 and the lamp holder 152. Moreover, the air will be heated by the ultraviolet lamp tube 151 after entering the reflector 16, which can further improve energy utilization rate and reduce power consumption by utilizing the heat generated by the ultraviolet lamp tube 151. Through arranging the reflector 16, the utilization rate of the light emitted by the ultraviolet lamp tube 151 is improved. The reflector 16 is arranged on the air inlet path of the fan 13, and the airflow hole is arranged on the reflector 16, then the airflow will enter the fan 13 through the reflector 16 and then be blown out, thus the ultraviolet lamp tube 151 may be cooled and the service life of the ultraviolet lamp tube 151 may be improved. Further, the heat generated by the ultraviolet lamp tube 151 may be used to heat the airflow at the inlet of the fan 13 to improve the energy utilization rate and reduce the energy consumption.

In an embodiment, the air inlet 114 is located at a position corresponding to the heater 12, so a part of the air will go to the fan 13 via the reflector 16, and the other part of the air may enter the heater 12 directly from the bottom of the shell 11 for heating, so as to reduce the air resistance and ensure that the fan 13 has sufficient air output.

In an embodiment, a side of the reflector 16 close to the fan 13 is provided with an airflow hole 163, so that the air is easier to enter the fan 13 from the airflow hole 163 after entering the reflector 16, so as to reduce the air resistance. Of course, in some other embodiments, the airflow holes 163 may be provided on both sides of the reflector 16. In still other embodiments, the airflow hole 163 may be provided at the side of the reflector 16 away from the fan 13.

In an embodiment, the reflector 16 includes two reflective side plates 162 and a support plate 161, and the airflow holes 163 are arranged on the reflective side plates 162. The support plate 161 is connected with the upper sides of the two reflective side plates 162. When used, the two reflective side plates 162 are located at both sides of the lamp holder 152, such that the two reflective side plates 162 are located at both sides of the ultraviolet lamp tube 151 when the ultraviolet lamp tube 151 is mounted on the lamp holder 152, so as to reflect the light. The distance between the two reflective side plates 162 is gradually enlarged from the support plate 161 to the direction facing away from the support plate 161. On the one hand, the light emitted by the ultraviolet lamp tube 151 may be reflected, and on the other hand the reflected light may be ensured to cover a relatively large area.

In an embodiment, the reflector 16 may be formed by stamping a metal plate to facilitate processing and manufacturing. In addition, the reflector 16 may also be used to cool the ultraviolet lamp tube 151. Of course, in some embodiments, the reflector 16 may also be a plastic cover, and a reflective coating is arranged on an inner surface of the plastic cover.

In an embodiment, the lower end of the reflective side plate 162 may be fixed at the bottom of the shell 11 to mount the reflector 16 in the shell 11.

In an embodiment, the support plate 161 of the reflector 16 may be fixedly connected with the lamp holder 152, and the lamp holder 152 may be fixed in the shell 11, so as to support the reflector 16 through the lamp holder 152.

In still some other embodiments, the lower end of the reflective side plate 162 may be fixed at the bottom of the shell 11, and the support plate 161 of the reflector 16 is fixedly connected with the lamp holder 152 to ensure the mounting stability of the reflector 16.

In an embodiment, the heater 12 is arranged between the fan 13 and the reflector 16, and the heater 12 is located at the inlet of the fan 13. In this way, the air enters the heater 12 for heating after preheated by the reflector 16, and then enters the fan 13. This structure can better heat the air, improve the energy utilization rate, and make the power of the heater 12 smaller.

In an embodiment, the main machine 10 further includes a grille window 153 detachably mounted at the bottom of the shell 11 and covering the window 115 so as to protect the ultraviolet lamp tube 151 in the reflector 16, and the light is transmitted and the air is ventilated through the grille window 153.

In an embodiment, the grating window 153 may use a light transmitting material so that the light emitted by the ultraviolet lamp tube 151 may be emitted through the grating window 153 to improve the light utilization rate.

The portable towel dryer 100 in the embodiments of the present application has the advantages of convenient use, small volume, large air volume, low energy consumption, high energy utilization rate, long service life, low cost, small weight and high strength.

The above has only described optional embodiments of the present application, and is not aimed to limit the present application. Any modification, equivalent substitution and improvement etc. made within the spirit and principle of the present application shall be included in the protection scope of the present application.

What is claimed is:

1. A portable towel dryer comprising a main machine and a rack configured to hang a cloth, wherein the main machine comprises a shell, a heater mounted in the shell and a fan mounted in the shell, an air outlet is provided at a bottom of the shell corresponding to an outlet of the fan, the bottom of the shell is provided with an air inlet, and the heater is arranged on an airflow path of the fan, wherein the rack comprises a hanging rod, two supports respectively supporting both ends of the hanging rod, and a lifting mechanism configured to adjust the height of the supports, each of the supports is connected with the lifting mechanism, and the lifting mechanism is connected with the shell; and wherein the lifting mechanism comprises a reinforcing plate connected with each of the supports respectively and a locking component configured to lock the reinforcing plate in the shell, the locking component is mounted on the shell, an upper end of the reinforcing plate is slidably inserted into the shell, and the bottom of the shell is provided with a lack for slidable insertion of an upper end of the reinforcing plate therein.

2. The portable towel dryer according to claim 1, wherein, the reinforcing plate is provided with a plurality of clamping slots, and the plurality of clamping slots are distributed on the reinforcing plate along a vertical direction at an interval; the locking component comprises a latch configured to fit into the clamping slot, a supporting shaft configured to support the latch, a supporting block configured to support the supporting shaft, and an elastic member configured to elastically push the latch along an axial direction of the supporting shaft into the clamping slot, the elastic member is mounted in the supporting block, and the supporting block is mounted on the shell.

3. The portable towel dryer according to claim 2, wherein, the locking component further comprises a button configured to push the latch, the button is mounted on the supporting block, and the button and the elastic member are respectively located on the opposite sides of the latch.

4. The portable towel dryer according to claim 3, wherein, the supporting block is arranged in the shell, and the shell is provided with a through hole configured to expose the button.

5. The portable towel dryer according to claim 2, wherein, a receiving groove is arranged in the supporting block, the latch is located in the receiving groove, and opposite two side walls of the receiving groove support the two ends of the supporting shaft respectively.

6. The portable towel dryer according to claim 1, wherein, each of the supports is provided with a support section, and a vertical section configured to support a wall, a lower end of the vertical section is fixedly connected with a rear end of the support section, the end of the hanging rod is supported on the corresponding support section, an upper end of the reinforcing plate extends out the vertical section, and each of the jacks is located at a corresponding position close to a rear side of shell.

7. The portable towel dryer according to claim 2, wherein, each of the supports is provided with a support section, and a vertical section configured to support a wall, a lower end of the vertical section is fixedly connected with a rear end of the support section, the end of the hanging rod is supported on the corresponding support section, an upper end of the reinforcing plate extends out the vertical section, and each of the jacks is located at a corresponding position close to a rear side of shell.

8. The portable towel dryer according to claim 3, wherein, each of the supports is provided with a support section, and a vertical section configured to support a wall, a lower end of the vertical section is fixedly connected with a rear end of the support section, the end of the hanging rod is supported on the corresponding support section, an upper end of the reinforcing plate extends out the vertical section, and each of the jacks is located at a corresponding position close to a rear side of shell.

9. The portable towel dryer according to claim 4, wherein, each of the supports is provided with a support section, and a vertical section configured to support a wall, a lower end of the vertical section is fixedly connected with a rear end of the support section, the end of the hanging rod is supported on the corresponding support section, an upper end of the reinforcing plate extends out the vertical section, and each of the jacks is located at a corresponding position close to a rear side of shell.

10. The portable towel dryer according to claim 5, wherein, each of the supports is provided with a support section, and a vertical section configured to support a wall, a lower end of the vertical section is fixedly connected with a rear end of the support section, the end of the hanging rod is supported on the corresponding support section, an upper end of the reinforcing plate extends out the vertical section, and each of the jacks is located at a corresponding position close to a rear side of shell.

11. The portable towel dryer according to claim 6, wherein, the support section is arranged as inclined downward in a direction from the rear side of the shell to a front side of the shell.

12. The portable towel dryer according to claim 1, wherein, the main machine further comprises an ultraviolet light source, and the ultraviolet light source is supported on the shell.

13. The portable towel dryer according to claim 2, wherein, the main machine further comprises an ultraviolet light source, and the ultraviolet light source is supported on the shell.

14. The portable towel dryer according to claim 3, wherein, the main machine further comprises an ultraviolet light source, and the ultraviolet light source is supported on the shell.

15. The portable towel dryer according to claim 4, wherein, the main machine further comprises an ultraviolet light source, and the ultraviolet light source is supported on the shell.

16. The portable towel dryer according to claim 5, wherein, the main machine further comprises an ultraviolet light source, and the ultraviolet light source is supported on the shell.

17. The portable towel dryer according to claim 12, wherein, the ultraviolet light source is an ultraviolet lamp tube, the main machine further comprises a lamp holder mounted in the shell, and a window exposing the ultraviolet lamp tube is arranged at the bottom of the shell.

* * * * *